United States Patent [19]

Thorne et al.

[11] Patent Number: 6,010,899
[45] Date of Patent: Jan. 4, 2000

[54] HIGH MOLECULAR WEIGHT PULLULAN AND METHOD FOR ITS PRODUCTION

[75] Inventors: Linda P. Thorne, Palomar; Thomas J. Pollock, San Diego; Richard W. Armentrout, La Jolla, all of Calif.

[73] Assignees: Shin-Etsu Bio, Inc., San Diego, Calif.; Shin-Etsu Chemical Co., Ltd., Tokyo, Japan

[21] Appl. No.: 07/841,707

[22] Filed: Feb. 26, 1992

Related U.S. Application Data

[62] Division of application No. 07/777,151, Oct. 16, 1991, Pat. No. 5,268,460.

[51] Int. Cl.[7] ........................................ C12N 1/14
[52] U.S. Cl. .................... 435/254.1; 435/911; 536/123.1
[58] Field of Search ................................ 435/254.1, 911; 536/123.1

[56] References Cited

U.S. PATENT DOCUMENTS 3,931,146  1/1976  Kato et al. ................................. 536/1.1
5,019,514  5/1991  Böck et al. ............................... 435/254

OTHER PUBLICATIONS

Leathers et al, *Journal of Industrial Microbiology*, vol. 3, (1988) pp. 231–239.
Kelly et al, *Journal of General Microbiology*, vol. 101 (1977) pp. 249–254.
Shumin NA, *Weishengwuxue Tongbao*, vol. 17 (1990) pp. 7–9.
Wickerham et al, *Mycologia*, vol. 67 (1975) 342–361.

*Primary Examiner*—Elli Peselev
*Attorney, Agent, or Firm*—McAulay Nissen Goldberg Kiel & Hand, LLP

[57] ABSTRACT

A method for obtaining a substantially biologically pure culture strain of *Aureobasidium pullulans* from a wild type strain by enriching the collected strain for organisms which grow as fungal yeastlike cells, growing colonies from isolated yeastlike cells and selecting those yeastlike cells which exhibit reduced pigmentation. Biologically pure culture strains obtained by the invention as well as methods for producing pullulan having decreased pigmentation and/or increased molecular weight are disclosed.

2 Claims, 5 Drawing Sheets

(AP1)

(AP2)

(AP11)

AP27)

(AP 30)

(AP 41)

(AP 42)

HIGH MOLECULAR WEIGHT PULLULAN AND METHOD FOR ITS PRODUCTION

This is a division of application Ser. No. 07/777,151, filed Oct. 16, 1991, now U.S. Pat. No. 5,268,460.

BACKGROUND OF THE INVENTION

Pullulan is a viscous water-soluble neutral polysaccharide having diverse applications. Its uses include: transparent films; oxygen-impermeable, tasteless, odorless coatings for food; viscosity control agents; adhesives for construction materials; fibers; and di-electrical materials in the form of cyanoethylpullulan. The purity of the polymer and molecular weight are important properties for the end uses.

Pullulan is an exopolysaccharide secreted by the fungus *Aureobasidium pullulans* (hereinafter referred to as *A. pullulans*) (Bernier, B., 1958, *Canadian Journal of Microbiology* 4:195–204; Bender, H. et al., 1959, *Biochimica et Biophysica Acta* 36:309–316). Several other similar isolates from nature also secrete pullulan (see comprehensive review by Catley, B. J., 1979, in *Microbial Polysaccharides and Polysaccharases*, R. C. W. Berkeley, G. W. Gooday and D. C. Ellwood [eds.] Academic Press).

*A. pullulans* is included in the American Type Culture Collection under one genus and species designation. The fungus is commonly isolated from forest litter, natural waters, industrial waste waters, paint surfaces, plastic, wood, leather, plant surfaces and canvass, and as an opportunistic pathogen from certain patients.

*A. pullulans* is a polymorphic fungus. Three distinctive forms predominate: elongated branched septate filaments, large chlamydospores and smaller, elliptical yeast-like single cells. Each of the three forms can be seen both in liquid media and on solid agar surfaces as part of a single colony.

An undesirable characteristic feature of *A. pullulans* is that it produces a dark pigment which is a melanin-like compound, and appears dark green to black in color.

The pigment contaminates the pullulan due to coprecipitation during recovery of the product. This pigmentation requires that the pullulan be subjected to a multistep decoloration treatment with activated charcoal followed by filtration to remove the pigment before the pullulan can be used. This understandably increases the cost and complexity of manufacture of products from pullulan. See U. S. Pat. No. 3,959,009 and U.S. Pat. No. 4,004,977.

Another undesirable characteristic of *A. pullulans* is that as the submerged growth of the organism in a fermentation progresses, the culture viscosity decreases due to a decrease in the average molecular weight of the accumulated extracellular pullulan. (Catley, B. J., 1970, FEBS Letters 10:190–193; Kaplan, D. L., B. J. Wiley, S. Arcidiacono, J. Mayer, and S. Sousa, 1987, *Materials Biotechnology Symposium Proceedings*, U.S. Army, Natick: 149–173).

U.S. Pat. No. 3,912,591 discloses that the initial culture conditions, e.g., pH, phosphate concentration, carbon source, inoculum size and time of harvest, affect the average molecular size of the polymer and yield of pullulan product. This patent further discloses that increasing the initial pH to 7 or higher results in a decrease in the molecular weight of the pullulan product.

SUMMARY OF THE INVENTION

We have discovered novel pure strains of *A. pullulans* which produce decreased amounts of pigment. We have further discovered a method for selecting the inventive pure strains; a method for making pullulan which is sufficiently non-pigmented so as to require little or no decolorization for use; and a method for making such pullulan having an average molecular weight in excess of about $8 \times 10^5$, as well as the pullulan made by the inventive processes.

More particularly, we have discovered that the pigment production characteristic of *A. pullulans* is associated mainly with the filamentous form and chlamydospores. We have further discovered that wild-type strains of *A. pullulans* obtained, for example, from depositories or natural sources, can be treated to enrich the fraction of yeast-like cells therein, and the yeast-like cells can be separated from the non-yeast-like cells. The separated yeast-like cells may then be grown and colonies can then be visually isolated based on their degree of pigmentation. The isolated colonies may then be subjected to further purification, if desired, and tested to measure and further isolate the strain producing the least amount of pigment when subjected to fermentation conditions. It is also desirable to measure the pullulan yields of the isolated colonies so that the strain having the maximum product yield as well as the minimum pigment production can be determined.

In accordance with the invention, pullulan of very high molecular weight may be obtained by subjecting *A. pullulans* to fermentation conditions and neutralizing the fermentation broth to a pH value of about 7 after the fermentation broth has stabilized at its characteristic low pH.

In yet another embodiment of the production method, pullulan of very high molecular weight may be obtained by subjecting *A. pullulans* to fermentation conditions and heat treating the accumulated pullulan for a time period and at a temperature sufficient to deactivate any pullulan decomposing enzymes in the accumulated pullulan.

By these methods, a novel pullulan product having an average molecular weight in excess of about $4 \times 10^6$ may be obtained and this can be accomplished without adversely affecting the yield. When the inventive pure strain is used as the production culture, a pullulan product having both high molecular weight and minimal pigmentation is obtained. The inventive pullulan exhibits a high viscosity and is particularly suitable for use in films, fibers, and as a rheology control agent for a variety of materials.

DETAILED DESCRIPTION OF THE INVENTION

Figure 1A:
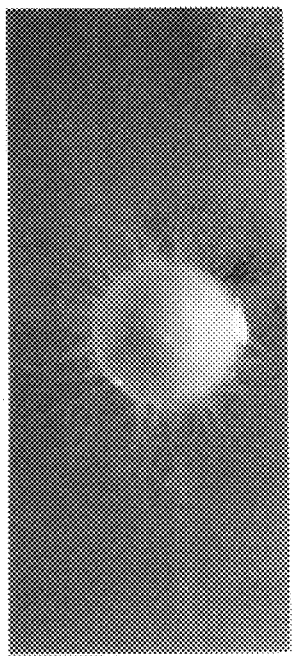
FIGS. 1A, 1B, 1C, 1D, 1E, 1F and 1G are photomicrographs showing colony morphologies of strains described herein.

Leaves were sampled from different species of trees located at various sites within San Diego County, Calif.

A culture enriched with yeast-like cells of *A. pullulans* was prepared by soaking a leaf from each plant in sterile water for three days at 25° C. and then transferring 0.1 ml to 10 ml of P2 minimal salts medium at pH 4 containing 1% (w/v) corn syrup and chloramphenicol at 10 micrograms/ml. After 2 days of shaking at 25° C., the turbid culture was allowed to sit undisturbed for 20 minutes to allow filaments and aggregates to settle to the bottom. "P2 minimal salts" medium contains, per liter of final volume: 2 g $K_2HPO_4$, 1 g $(NH_4)_2HPO_4$, 0.5 g NaCl, 0.05 g $MgSO_4\text{-}7H_2O$, 0.01 g each of $FeSO_4$, $MnSO_4$ and $ZnSO_4$, and deionized water. The pH of this medium is adjusted to pH 4 with 6N HCl, and then autoclaved and cooled.

Upon settling, an upper partially clarified phase was obtained which was enriched in yeast-like cells. About 10 ml of this phase was spread onto agar plates containing P2 minimal salts medium adjusted to pH 5, 1% (w/v) corn syrup and chloramphenicol at 10 mg/ml. Corn syrup is added to 10–50 g/l (dry weight/volume). (Corn syrup is readily available, e.g., Globe 1632, Corn Products, a unit of CPC North America, 82.5% dry substance, 43.2 Baume and 63–66 dextrose equivalent; Hubinger of Keokuk, Iowa; 43 Baume, 63 dextrose equivalents and 81% dry substance.) Agar was included at a concentration of 15 g/l (for solid plates).

After four days, independent colonies were purified by replating and tested in shake flasks for secretion of isopropylalcohol-precipitable polysaccharides and culture pigmentation. One isolate from each plant was selected for further study based on yield of polysaccharide and low pigmentation. The strains isolated were identified with numbers beginning with the prefix AP and are listed in Table 1 along with the identity and location of the plant source for each.

TABLE 1

| Designation | PLANT SOURCE | LOCATION State of California |
|---|---|---|
| AP11 | *Ficus rubiginosa* | Sorrento Mesa |
| AP30 | *Acacia sp.* | La Jolla |
| AP31 | *Nerium oleander* | La Jolla |
| AP32 | *Liqidamber syraciflua* | La Jolla |
| AP33 | *Quercus kelloggi* | Palomar Mountain |
| AP34 | *Raphiolepis indica* | University City |
| AP35 | *Vitis vinifera* | University City |
| AP36 | *Magnolia grandiflora* | University City |
| AP24 | Ethidium-treated derivative of AP11 | |
| AP41 | Ethidium-treated derivative of AP24 | |
| AP26 | *Ficus rubiginosa* | Sorrento Mesa |
| AP27 | *Ficus rubiginosa* | Sorrento Mesa |
| AP42 | Ethidium-treated derivative of AP30 | |

The following strains have been deposited with the American Type Culture Collection at 12301 Parklawn Drive, Rockville, Md. 20852, U.S.A., on Sep. 30, 1991, pursuant to the Budapest Treaty on the International Recognition of the Deposit of Microorganisms for the Purposes of Patent Procedure and were confirmed as viable on this date. All restriction on the availability of the strains deposited hereunder shall be revoked upon the issuance of a U.S. Patent based on this application.

| | | ATCC Designation |
|---|---|---|
| AP11 | *Aureobasidium pullulans* | 74100 |
| AP24 | *Aureobasidium pullulans* | 74101 |
| AP27 | *Aureobasidium pullulans* | 74102 |
| AP41 | *Aureobasidium pullulans* | 74103 |

-continued

| | | ATCC Designation |
|---|---|---|
| AP42 | *Aureobasidium pullulans* | 74104 |
| AP30 | *Aureobasidium pullulans* | 74105 |

Preexisting strains used for comparisons were obtained from public culture collections as listed in Table 2:

TABLE 2

| Designation | Access Code | Source |
|---|---|---|
| AP1 | IF04464 | Fermentation Institute, Osaka, Japan[1] |
| AP2 | IF06353 | Fermentation Institute, Osaka, Japan[1] |
| AP3 | QM3092 | ATCC 9348[2] |
| AP4 | NRRL Y6220 | ATCC 34647[3] |
| AP5 | NRRL Y12996 | ATCC 42023[4] |
| AP7 | S-1 | NRRL Y17005[5] |
| AP9 | — | NRRL Y12974[6] |

[1] K. Kato and M. Shiosaka. October 1975. Process for the Production of Pullulan. U.S. Patent 3,912,591.
[2] B.J. Catley 1979, Pullulan Synthesis by *Aureobasidium pullulans*, p. 69–84. In R.C.W. Berkeley, G.W. Gooday, and D.C. Ellwood (eds.), Microbial Polysaccharides and Polysacchareses, Acad. Press, London.
[3] D.L. Kaplan, B.J. Wiley, S. Arcidiacono, J. Mayer, and S. Sousa, 1987. Controlling biopolymer molecular weight distribution: pullulan and chitosan, p. 149–173. In D.L, Kaplan (ed.), Materials Biotechnology Symposium Proceedings. U.S. Army, Natick.
[4] J.E. Zajic and A. Leduy. 1973. Flocculant and chemical properties of a polysaccharide from *Pullularia pullulans*. Appl. Microbiol. 25:628–635
[5] S. Ueda, K. Fujita, K. Komatsu, and Z. Nakashima. 1963. Polysaccharide produced by the genus Pullularia. Appl. Microbiol. 11:211–215.
[6] T.D. Leathers, 1986. Color Variants of *Aureobasidium pullulans* overproduce xylanase with extremely high specific activity. Appl. Environ. Microbiol. 52:1026–1030.

Of the strains listed in Table 1, Strain Nos. AP11, AP26, AP27, AP30, AP31, AP32, AP33, AP34, AP35, and AP36, were natural isolates. All of the strains listed in Table 1 were similar in appearance when cultured on agar plates containing minimal salts and a sugar, such as, P2 medium (described above) or P1 medium. P1 medium contains, per liter of deionized water: 2 g yeast extract (Difco), 0.5 g $(NH_4)_2SO_4$, 1 g NaCl, 0.2 g $MgSO_4$, 3 g $K_2HPO_4$, 0.01 g each of $FeSO_4$, $MnSO_4$ and $ZnSO_4$, and HCl to pH 6.0. The sugar was either sucrose or corn syrup to give a final concentration of from 1–5% (g dry weight per 100 ml) and the agar was 15 g per liter of medium. After three to five days, the colonies were shiny, off-white to slightly pinkish in color and showed varying degrees of filamentation. Strains AP31, AP32, AP33, AP34, AP35 and AP36 were eliminated from further study based on lower yield, darker pigmentation in shake flask cultures and lower viscosities per gram of IPA-precipitable polysaccharides. The eliminated strains were compared to the other strains existing at the time: AP11, AP24, AP27 and AP30. Specifically, AP31 showed darker pigment and lower viscosity per gram. AP32 and AP35 both showed lower yield and lower viscosity per gram. AP33 and AP36 both showed light pigmentation and lower viscosity per gram. AP34 showed light pigmentation.

Figure 1B:
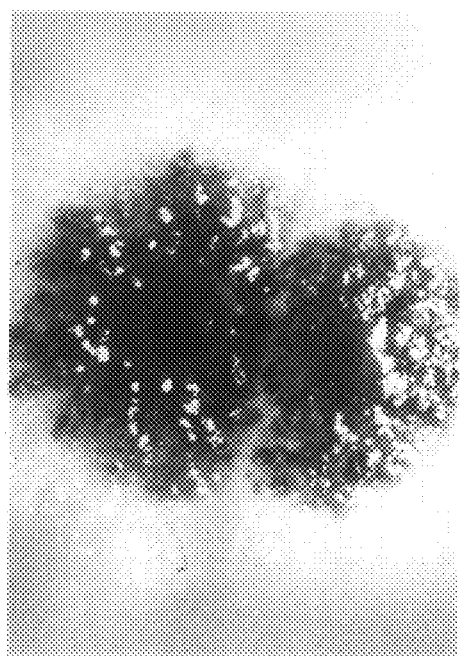
Figure 1C:
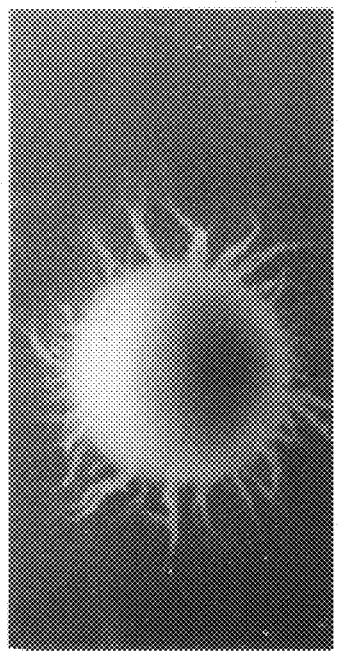
Figure 1D:
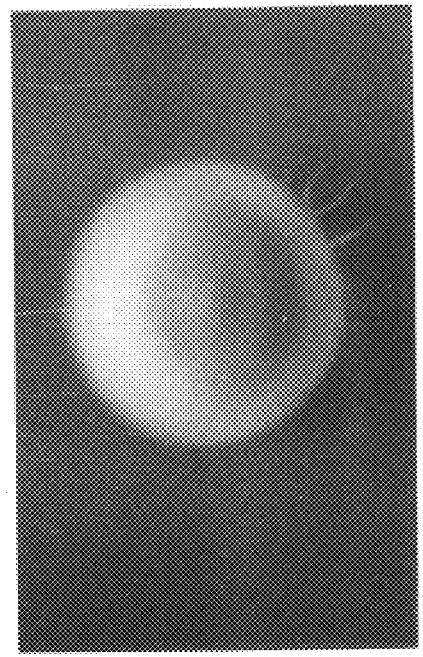
Figure 1E:
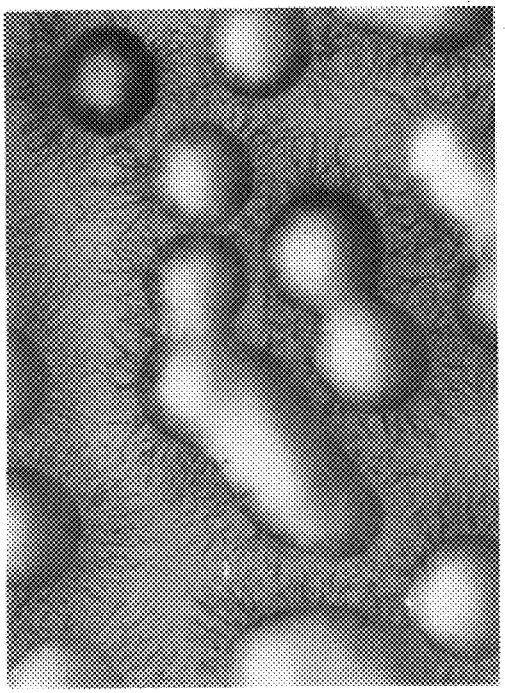
Figure 1F:
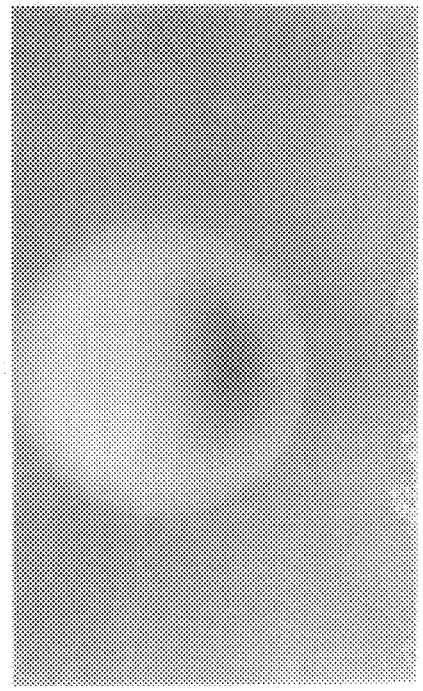
Figure 1G:
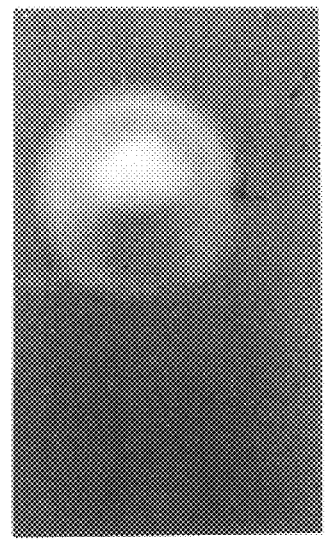

With the exception of strains AP2 and AP7, colonies of the preexisting strains (AP1 to AP9) and the new isolates described here (AP11 to AP42) were similar in general appearance when grown on P1 or P2 containing agar plates. FIGS. 1A and 1B are photomicrographs showing the colony morphologies of preexisting isolates AP1 and AP2, respectively. FIGS. 1C, 1D, 1E, 1F, and 1G are photomicrographs showing the colony morphology of inventive strains AP11, AP27, AP30, AP41 and AP42, respectively. After incubation for three days at 28° C., colony colors ranged from off-white or light beige to faintly pink or salmon-colored and the colony diameters varied from about 1 to 3 mm. Branched septate filaments extended from the center of each colony to beyond the edge of a glistening raised semi-round zone of yeast cells, and also down into the agar. The densities and radial extent of the filaments were different among the strains. For example, new strain AP27 was the least pigmented of the natural isolates and formed the fewest filaments. The colonies continually expanded for about ten days or until the plates became dry. After about four days of growth at 28° C. some of the filaments began to accumulate an olive-colored pigment that appeared to blacken with age. If exposed to the light-dark cycle of the fluorescent room light, concentric rings of pigmentation developed. Strains AP2 and AP7 became exceptionally dark. The filamentous zones for all strains eventually accumulated at least some of the dark pigment, and sometimes appeared sectored. The new strains were most similar to AP9 (Y12974) which was isolated from Florida sea grass. T. T. Leathers, 1986. Color Variants of Aureobasidium pullulans overproduce xylanase with extremely high specific activity. Appl. Environ. Microbiol. 52:1026–1030. AP27 appeared nonpigmented and grew predominantly in the yeast form. Although strain AP1 was more pigmented than AP27, it was isolated from a different leaf the same plant as AP27.

Since A. pullulans is polymorphic on agar plates or in submerged liquid culture, positive identification of the fungus with the unaided eye is difficult. Microscopic observations of the new isolates revealed the same three predominant types of cells seen for the preexisting strains, i.e., budding yeastlike cells, branched filaments and chlamydospores which are pigmented cells about twice the size of the yeast forms. In submerged liquid culture the new isolates appeared similar to strains AP1, AP3, AP4, AP5 and AP9, but unlike strains AP2 and AP7 which were more highly pigmented. In the latter case, the medium turned black, so that after precipitation with isopropyl alcohol the pullulan was dark olive in color. The less pigmented cultures were various shades of light yellow, olive-grey and combinations thereof, and gave rise to pullulan with an off-white tint. For a given strain, the intensity and color can change based on the culture conditions: nitrogen source and concentration, carbon source and concentration, phosphate concentration, initial pH, aeration, inoculum source and amount, trace minerals and temperature. These parameters may be easily varied to minimize the intensity and color obtained for the particular strain. In the examples that follow, these variables were held constant for meaningful comparisons of color. Isolate AP27 produced the least pigment in liquid culture, and the IPA-precipitated pullulan was white.

Several of the natural isolates were treated with ethidium bromide. In particular, strain AP24 was obtained from Strain AP11, a natural isolate whose colonies appeared less pigmented compared to strains AP1 to AP9. AP11 was grown in 10 ml of P1 medium with 5% w/v sucrose to a density of about 4–5×10$^6$. Ethidium bromide (30 μl from a 10 mg/ml solution in 25% v/v ethanol in water) was added and shaking continued for 3–4 hours at about 25° C. During this period, the cells tripled in number. The treated cells were centrifuged (5000×g for 5 min), washed with deionized water, recentrifuged and the cell pellet was suspended in 30 ml of P1 medium with 15% v/v glycerol replacing the sugar and lacking yeast extract and $(NH_4)_2SO_4$. The cells were stored 4 days at 4° C. and then plated on selective medium. A sample of the treated cells were diluted by about 10$^4$ in the same solution and spread onto agar plates containing P1 medium with Pharmamedia (a cottonseed extract from Trader's Co.) at 0.2% w/v replacing yeast extract, 0.025% w/v $(NH_4)_2SO_4$, 0.2% w/v glucose and buffered to pH 7. The inclusion of Pharmamedia enhances pigment formation. Several morphologically distinct colonies were picked from the plates after 3–6 days and purified by restreaking. The altered phenotypes included colonies with more filaments and others with more yeast-like cells, as well as colonies with different degrees of pigmentation. Strain AP24 was selected for further study as a mutant with predominantly yeast-like cells and less pigment.

A modification of the above method was used to isolate strain AP42. AP30 was treated with ethidium bromide as described above. The treated cells were then exposed to a low dose of ultraviolet light from a Sylvania 8 watt germicidal lamp (G8T5) from a distance of 10 cm for 15 sec. This dose causes a survival frequency for A. pullulans of greater than 20% and less than 50%. The treated cells were spread on agar plates containing P1 medium with 0.5% w/v Pharmamedia replacing yeast extract, 1% sucrose and buffered to pH 7. After 3–5 days incubation at 25° C., less-pigmented colonies were picked and restreaked to purify.

Liquid cultures of 15 ml of P2 medium containing 5% corn syrup in 125 ml baffled Erlenmeyer flasks were inoculated with seven purified isolates. Of these seven, two cultures remained nonpigmented after 4 days of shaking at 25° C. Of the two, AP42 was the most viscous, as judged by inverting the flask and observing the velocity of flow of the culture. Strain AP41 was derived by first growing strain AP24 to late log phase to a cell density approximating 10$^8$ cells per ml in P2 medium plus 1% (w/v) sucrose. The cells were washed two times by centrifugation and resuspension in P2 minimal salts with nitrogen and without a carbon source. About 10$^5$ cells were spread on a P2 minimal salts agar plate lacking nitrogen but with 2.5% (w/v) sucrose. The plate was exposed to ultraviolet light from a Sylvania 8 watt germicidal lamp (G8T5) from a distance of 10 cm for 90 sec, and then placed in the dark for 18 hr at 25° C. Ammonium sulfate was added to the plate to a final concentration of 0.1% (w/v) and the incubation continued for 40 hr. The surface of the plate was overlayered with 5 ml of 1.5% (w/v) warm agar containing nystatin (Sigma Chemical) at 25 units per ml., and then incubated 18 hours at 25° C. The surface of the plate was then overlayered with 5 ml of 1.5% (w/v) agar containing yeast extract (0.2% w/v) and casamino acids (0.1% w/v). After several days, a few colonies of A. pullulans appeared. One, AP41, was saved because of its non-pigmented and more yeast-like colonial appearance compared to the parent AP24.

The strains thus obtained were analyzed for their restriction patterns of DNA. The strains were also tested for pullulan production, and the pullulan obtained was analyzed for molecular weight by correlation with viscosity, and polysaccharide composition.

Figure 4:
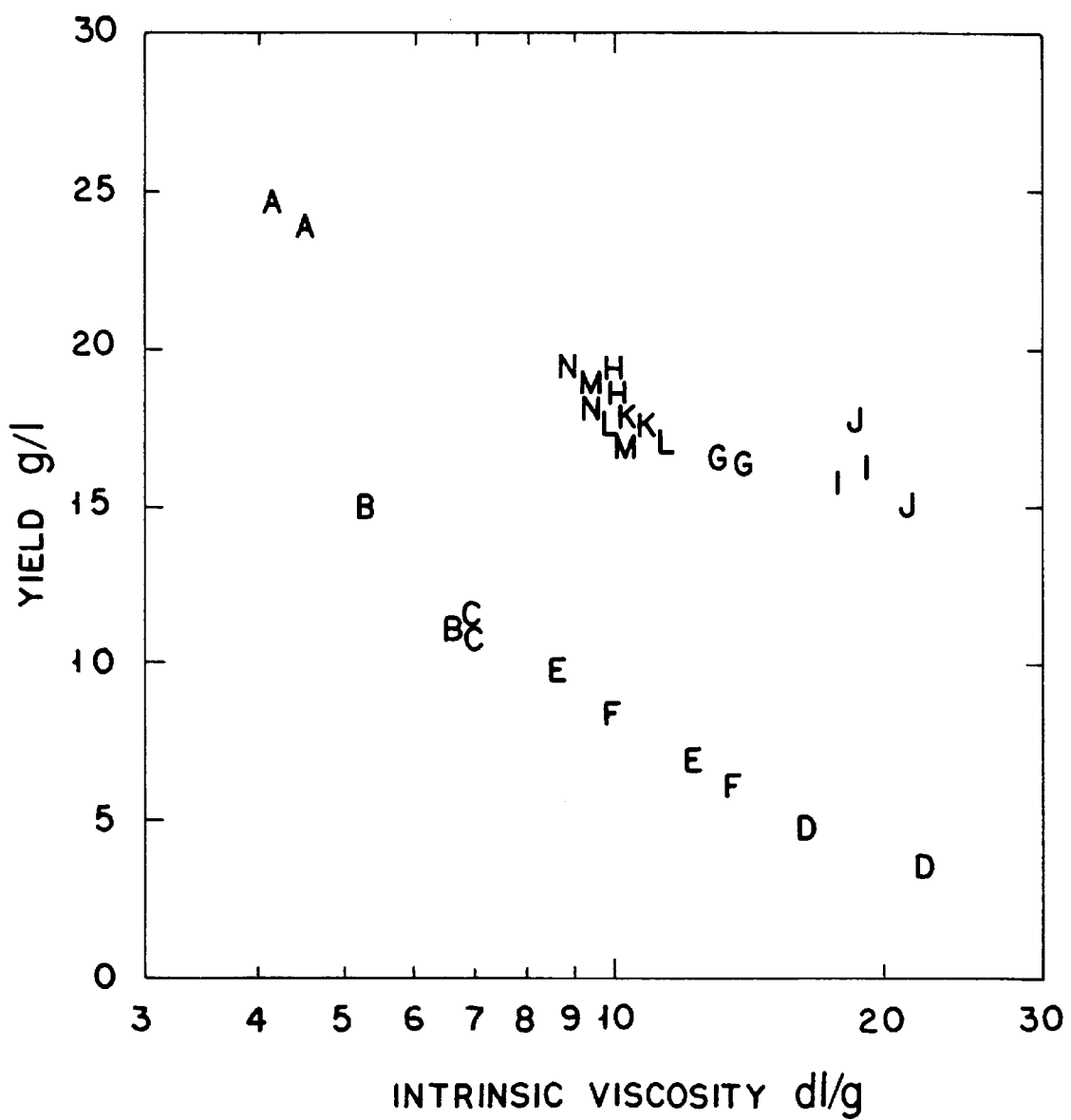
FIG. 4 is a graph showing variation of viscosity with yield.

We have also found new methods for the fermentation of A. pullulans which provide relatively high yields of high molecular weight pullulan. Thus, with the inventive fermentation method, pullulan of a molecular weight in excess of about 4×10$^6$ can be obtained. In particular, we have discovered procedures for avoiding the decrease in the molecular weight of the accumulated pullulan in the fermentation broth that is normally observed during the submerged growth of A. pullulans. In particular, pullulan having an average molecular weight in excess of 1×10$^6$, 2×10$^6$, 4×10$^6$ and even 6×10$^6$ can be obtained with the inventive process. Indeed, as shown in FIG. 4 referred to hereinafter, average intrinsic viscosities corresponding to $M_w$ in the range from about 8 to 15×16$^6$ are observed. In addition, by using the inventive strains, high molecular weight pullulan which is substantially non-pigmented can be obtained. As used herein, "substantially non-pigmented pullulan" means pullulan which, as harvested from the fermentation broth, does not require decolorization treatment for its further use. "Decolorization treatment" does not include simple washing.

The first procedure comprises adjusting the pH of the fermentation broth to a neutral value at a stage of the fermentation when the natural pH decrease has stabilized. In carrying out the inventive method, the fermentation is initiated in the conventional manner known in the art. We have observed that after an initial start-up period, typically, about 24–36 hours, the pH of the broth stabilizes at a value of about 3.5–4.0 and the fermentation proceeds with the broth pH staying at this value. In accordance with the inventive method, after the pH has stabilized at this value, it is adjusted to a value of about 7 with an appropriate base. Suitable bases include any basic compound which will be effective to adjust the pH to a neutral value and which will not detrimentally affect the fermentation or product. For example, aqueous solutions of sodium hydroxide and the like may be used. After the pH adjustment, the fermentation proceeds in the normal manner to completion. However, the usual decrease in viscosity and concomitant product molecular weight, are not observed. Thus, using this inventive procedure, when the pullulan product is harvested, the molecular weight of the product is substantially higher than if the pH adjustment step was not carried out. The specific time of the pH adjustment may vary depending on the specific fermentation conditions used, but is easily determined using conventional techniques. We have found that it is best to effect the pH adjustment as early as possible in the fermentation after the pH has stabilized at its normal value, i.e., about 3.5–4.0. However, the pH adjustment can be made at other times during the fermentation process. For example, the broth viscosity can be monitored and the adjustment made at a time when the product molecular weight (as indicated by broth viscosity) is at a desired value. Similarly, product samples can be harvested and the size determined to provide a rapid indication of the product molecular size.

A second inventive procedure for avoiding the molecular weight decrease after fermenting the product is to subject the accumulated pullulan to treatment at an elevated temperature. The fermentation broth contains an enzyme, alpha-amylase, which is suspected to effect cleavage of subunits making up the pullulan (See Leathers, T. D., 1987. *Host Amylases and Pullulan Production*, Materials Biotechnology Symposium Proceedings, Kaplan, D. L. (ed.), U.S. Army Natick Research, Development and Engineering Center, pp 175–185; Carolan, G., Batley, G. J. and McDougal, F. J. 1983. *The Location of Tetrasaccharide Units in Pullulan*. Carbohydrate Research 114:237–243). This results in a decrease in the molecular weight of the pullulan as it accumulates in the fermentation broth and acts to limit the ability to obtain higher molecular weight pullulans. However, we have found that the accumulated high molecular weight pullulan can be harvested during the progress of the fermentation and heat treated exterior of the fermentation broth. This heat treatment serves to deactivate the enzyme adhered to the separated pullulan, thus preserving the high molecular weight of the product. Understandably, the heat treatment cannot be applied to the pullulan during the fermentation since this would kill the microorganisms and cause cessation of the fermentation. When the heating step in accordance with the invention is carried out, the pullulan product obtained from the fermentation possesses a molecular weight substantially the same as that at the time of the heat treatment.

The temperature used should be sufficiently high and the heating period long enough to deactivate the enzyme. These parameters depend on the specific fermentation procedure being used, i.e., strain, medium, and the like. However, it may be easily determined by a simple screening process. Generally, we have found that temperatures in the range from about 70 to 120° C., preferably, from about 80 to 100° C., for time periods from about 30 to 150 minutes, and preferably, from about 30 to 60 minutes, are suitable. The heat inactivation is carried out when the fermentation is judged to be complete, with respect to product yield and quality, such as the molecular weight and pigmentation, or when the carbon source is exhausted.

EXAMPLES

The following examples describe the analysis of the inventive strains, pullulan product obtained therefrom, and processes in accordance with the invention.

Example 1.
DNA Restriction Patterns of Inventive Strains

Cells were cultured overnight to mid-log phase in P2 medium with 1% w/v sucrose, concentrated by centrifugation (5000×g for 5 minutes), and resuspended at $10^9$ cells/ml in 1 M sorbitol, 25 mM EDTA and 25 mM dithiothreitol at pH 7.0. Following a second centrifugation, protoplasts were prepared by resuspending $2.5 \times 10^8$ cells for 15 minutes at 37° C. in 0.5 ml of a solution containing 1 M sorbitol, 25 mM EDTA and 2.5 mg lysing enzyme (from *Trichoderma harzianum*; Sigma). Following a third centrifugation, protoplasts were lysed by resuspension in 0.75 ml of 10×TE (50 mM Tris-HCl, 10 mM EDTA, pH 8) containing 1% (w/v) sodium dodecyl sulfate, and then immediately mixed with 0.5 ml of phenol:chloroform (1:1 and saturated with water) to reduce nucleolytic degradation. After centrifugation of the emulsion at 10,000×g for 2 minutes, the viscous upper phase was precipitated with 1 volume of isopropylalcohol at 4° C. for 10 minutes and centrifuged at 10,000×g for 10 minutes at 25° C. The precipitate was resuspended in 0.5 ml 1×TE containing 100 µg RNase A (Sigma) for 10 minutes at 25° C. and then extracted with 2 volumes phenol/chloroform, precipitated with isopropanol and finally resuspended in 0.11 ml 1×TE. The DNA was high molecular weight as seen by gel electrophoresis. DNA samples were digested to completion with EcoRI (Sigma) in 50 mM Tris-HCl, 10 mM $MgCl_2$, 50 mM NaCl and 0.1 mg bovine serum albumin (Sigma)/ml at pH 8, electrophoresed through 1% (w/v) agarose gel with Tris-acetate buffer and stained with ethidium bromide. T. Maniatis, F. Fritsch, and J. Sambrook. 1982. *Molecular cloning: a laboratory manual*. Cold Spring Harbor Laboratory, Cold Spring Harbor.

Figure 2A:
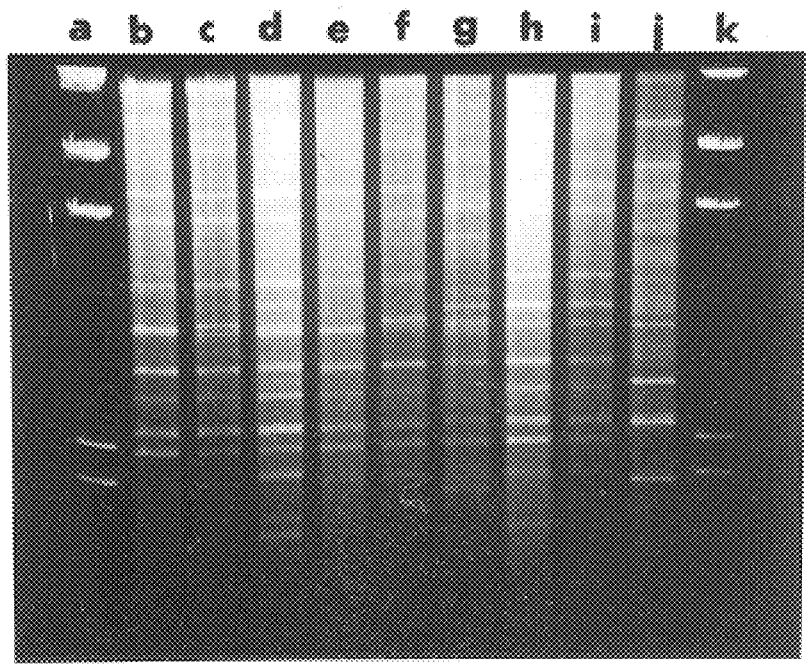
FIGS. 2A and 2B are photographs of DNA restriction gels.
Figure 2B:
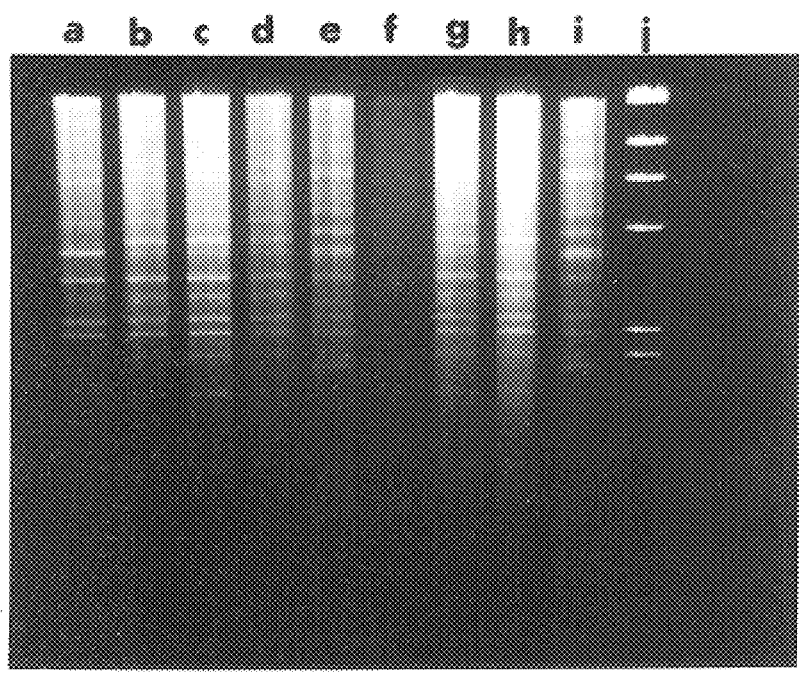

We confirmed the visual identifications and distinguished the new *A. pullulans* isolates from preexisting strains according to the pattern of restriction fragments generated from repetitive sequences of DNA as shown in FIGS. 2A and 2B.

For the DNA banding pattern of *Saccharomyces cerevisiae* (See P. Philippsen, A. Stotz, and C. Scherf. 1991. DNA of *Saccharomyces cerevisiae*, p. 169–182. In C. Guthrie and G. R. Fink (eds.), Guide to yeast genetics and molecular biology. Academic Press, San Diego.

For Candida and other eukaryotes, relatively dark bands of repeated DNA stand out over a background of fainter unique restriction fragments. B. B. Magee, T. M. D'Souza, and P. T. Magee. 1987. Strain and species identification by restriction fragment length polymorphisms in the ribosomal DNA repeat of Candida species. J. Bacteriol. 169:1639–1643. S. Scherer and D. S. Stevens. 1987. Application of DNA typing methods to epidemiology and taxonomy of Candida species. J. Clin. Microbiol. 25:675–679.

In FIG. 2A, lanes a and k are bacteriophage Lambda DNA digested with Hind III restriction endonuclease and lane b to i are A. pullulans DNA samples digested with EcoRI endonuclease. Lane b is strain AP1; c is AP2; d is AP3; e is AP4; f is AP7; g is AP9; h is AP11; i is AP30; and i is S. cerevisiae.

In FIG. 2B, lane a is strain AP1; b is AP1; c is AP24; d is AP30; e is AP31; f is AP33; g is AP34; h is AP35; i is AP32; and i is bacteriophage Lambda DNA digested with HindIII endonuclease. Samples in lanes a to i were digested with EcoRI endonuclease.

Five bands generated by EcoRI cleavage of DNA from S. cerevisiae were prominent and corresponded to the expected fragments of ribosomal DNA of 2.79, 2.46, 2.02, 0.66 and 0.59 kb (FIG. 2a, lane j). The additional expected bands at 0.35 and 0.22 kb migrated off the bottom of the gel. In FIG. 2a we compared the preexisting strains, AP1, AP2, AP3, AP4, AP7 and AP9, to our new strains AP11 and 30. The majority of bands appeared to be in the same relative positions, suggesting that all the strains were probably closely related. However, a few bands were unique. The banding pattern for AP1 appeared like AP4, strain AP2 was like AP7, and AP11 was like AP30. Likewise, in FIG. 2b we compared the other new strains to AP11 and AP30. Two patterns were evident: one for strains AP11, 24, 30, 33, 34, 35 and 36; and a different pattern for strains AP31 and AP32. Members of these two groups were found in close physical proximity: strains AP31 and AP32 were isolated from different plant species separated by only by about forty feet from AP30.

Example 2.
Pullulan Yield, Intrinsic Viscosity and Composition

Growth on Agar Plates

For each strain, a sample of cells was removed from the −70° C. freezer and spread on "P1s" agar plates containing (per liter final volume): 15 g Difco agar, 2 g Difco yeast extract, 3 g $K_2HPO_4$, 0.5 g $(NH_4)_2SO_4$, 1 g NaCl, 0.2 g $MgSO_4 \cdot 7H_2O$, 0.01 g each of $FeSO_4$, $MnSO_4$ and $ZnSO_4$. This medium was adjusted to pH 6.0 with HCl, then autoclaved and cooled to about 50° C. Finally, sucrose (autoclaved separately) was added to a concentration of 10 g/l. The plates were incubated at room temperature (about 22–24° C.) for 2–4 days.

Growth in Liquid Culture

A single colony or loopful of cells of strains AP1 and AP24 was added to 30 ml of "P2c" liquid medium containing (per liter final volume): 2 g $K_2HPO_4$, 1 g $(NH_4)_2HPO_4$, 0.5 g NaCl, 0.05 g $MgSO_4 \cdot 7H_2O$, and 0.01 g each of $FeSO_4$, $MnSO_4$ and $ZnSO_4$. The medium was adjusted to pH 7.0 with 6N HCl, then autoclaved and cooled. Finally, corn syrup was added to 50 g/l (dry weight per volume). In preliminary tests with strain AP24, the yield of polysaccharide was higher when corn syrup was used in place of sucrose. For strain AP30, the medium above was used, except that sucrose was substituted for the corn syrup. In preliminary tests, the molecular size of the polysaccharide made by strain AP30 was higher when sucrose was used in place of corn syrup. The culture was shaken at about 23–27° C. for 20–30 hours until the density reached about $1–5 \times 10^7$ cells/ml. The cell densities were measured microscopically and then $4 \times 10^8$ cells were used as the inoculum for 400 ml cultures in 1000 ml Erlenmeyer shake flasks with three baffles. These cultures were shaken for 64 hours at 23–27° C. at 200 rpm in a Labline shaker with a horizontal orbit diameter of ¾ inch.

Isolation of Polysaccharide

Each of the three cultures were diluted with an equal volume of deionized $H_2O$ and then centrifuged at $8,000 \times g$ for 8 minutes to remove cells. The supernatants were transferred to fresh tubes and centrifuged a second time. The centrifuged cultures were divided into aliquots of about 40 g each. (The samples were processed in aliquots to facilitate rehydration.) The extracellular polysaccharides in the twice-centrifuged supernatants were precipitated with 1 volume of isopropylalcohol (IPA) at room temperature. Most of the IPA was removed by pressing the clotted polysaccharides and then the remainder was removed by drying in an oven at 80° C. for about 16 hr. until constant weight was obtained. The dried clots from strain AP1 and AP30 were light tan in color, while that from AP24 was white. The precipitated material was kept at room temperature until use. For each sample, five of the dried clots were weighed to measure the yield of polysaccharide for each culture. For physical and chemical analysis, a sample of dried and weighed polysaccharide was dissolved in deionized $H_2O$ at room temperature with stirring at a final concentration of 1.0 g/100 ml and containing 0.01% (w/v) sodium azide. Samples of commercial pullulan from Hayashibara (PF-10 lot number 90201 and PF-20 lot number 90517) were also dried at 80° C. for 2 hours and then dissolved at 5.0 g/100 g with 0.01% sodium azide. Table 3 shows that the exopolysaccharide yields for the new strains are similar to that of the preexisting AP1.

TABLE 3

| Culture | Dry weight of IPA-precipitate (mg)/volume sampled (ml) | | | | | Culture yield g EPS/1 |
| --- | --- | --- | --- | --- | --- | --- |
| | Sample 1 | Sample 2 | Sample 3 | Sample 4 | Sample 5 | |
| AP1 | 265/12.5 | 265/12.5 | 270/12.5 | 266/12.5 | 544/25.0 | 21.4 |
| AP24 | 517/25.0 | 526/25.0 | 517/25.0 | 525/25.0 | 651/30.25 | 21.0 |
| AP30 | 458/25.0 | 466/25.0 | 455/25.0 | 451/25.0 | 601/33.0 | 18.2 |

Determination of Molecular Size

Viscosities in units of centipoise (cp) were measured for different dilutions of each sample at various shear rates using a UL adapter (for low viscosity solution) on a Brookfield DV-II viscometer. The viscosity ($\eta$) at a shear rate of 1 sec$^{-1}$ was determined from a mathematical "best fit" of the data using a linear regression. This viscosity value was also taken as the relative viscosity ($\eta_R$), where $\eta_R = \eta/\eta_0$, where $\eta_0 = 1$ for $H_2O$. A graph of $C^{-1} \ln \eta_R$ as a function of C was prepared with C expressed as g/dl. From the mathematical "best fit" to this line, the intrinsic viscosity [$\eta$] was taken as the y-intercept. The weight average molecular size ($M_W$) was calculated from the equation: $[\eta] = (0.000258)M_W 0.646$ where the units for intrinsic viscosity are expressed as dl/g (Buliga, G. S. and Brant, D. A., 1987, International Journal of Biological Macromolecules 9:71–76). Table 4 below shows that the new strains accumulate exopolysaccharide with higher molecular weight than the preexisting strain AP1.

TABLE 4

| Shear Rate | Polysaccharide concentration C (g/dl) | | | | | | | | | | | |
|---|---|---|---|---|---|---|---|---|---|---|---|---|
| | AP1 | | | | AP24 | | | | AP30 | | | |
| sec⁻¹ | 1.00 | 0.75 | 0.56 | 0.42 | 1.00 | 0.75 | 0.56 | 0.42 | 0.50 | 0.38 | 0.28 | 0.21 |
| 73.4 | 6.4 | 4.3 | 3.1 | 2.4 | | 6.9 | 4.6 | | 17 | 9.2 | 6.1 | 4.2 |
| 36.7 | 6.8 | 4.2 | 3.0 | 2.3 | 12 | 7.0 | 4.7 | | 17 | 10 | 6.5 | 4.4 |
| 14.7 | 6.7 | 4.3 | 3.0 | 2.2 | 23 | 12 | 7.0 | 4.6 | 20 | 11 | 6.8 | 4.6 |
| 7.34 | 7.1 | 4.7 | 3.1 | 2.3 | 23 | 12 | 7.0 | 4.7 | 21 | 12 | 7.1 | 4.8 |
| 3.67 | | | | | 23 | | | | | | | |
| 1.83 | | | | | 24 | | | | | | | |
| 0.73 | | | | | | | | | | | | |
| $C^{-1}\ln\text{-}\eta R$ | 1.97 | 2.12 | 2.00 | 1.81 | 3.18 | 3.17 | 3.50 | 3.70 | 26 | 15 | 8.1 | 5.4 |
| $[\eta]$ | | 1.8 | | | | 4.0 | | | | 9.0 | | |
| $M_w$ | | $0.9 \times 10^6$ | | | | $3.0 \times 10^6$ | | | | $11 \times 10^6$ | | |

| Shear Rate | Polysaccharide concentration C (g/dl) | | | | | | |
|---|---|---|---|---|---|---|---|
| | PF10 | | | PF20 | | | |
| sec⁻¹ | 5.0 | 3.75 | 2.81 | 5.0 | 3.75 | 2.81 | 2.11 |
| 73.4 | 5.1 | 3.4 | 2.6 | | 9.3 | 5.9 | 4.0 |
| 36.7 | 5.0 | 3.5 | 2.5 | | 9.3 | 5.8 | 4.0 |
| 14.7 | 4.9 | 3.3 | 2.4 | 17 | 9.2 | 5.8 | 3.9 |
| 7.34 | 5.0 | 3.4 | 2.6 | 18 | 9.4 | 5.8 | 4.0 |
| 3.67 | | | | 17 | | | |
| 1.83 | | | | 17 | | | |
| 0.73 | | | | | | | |
| $C^{-1}\ln \eta R$ | 0.32 | 0.32 | 0.32 | 0.57 | 0.60 | 0.62 | 0.65 |
| $[\eta]$ | | 0.32 | | | 0.7 | | |
| $M_w$ | | $0.06 \times 10^6$ | | | $0.2 \times 10^6$ | | |

Relation Between Intrinsic Viscosity and Molecular Weight

Figure 3:
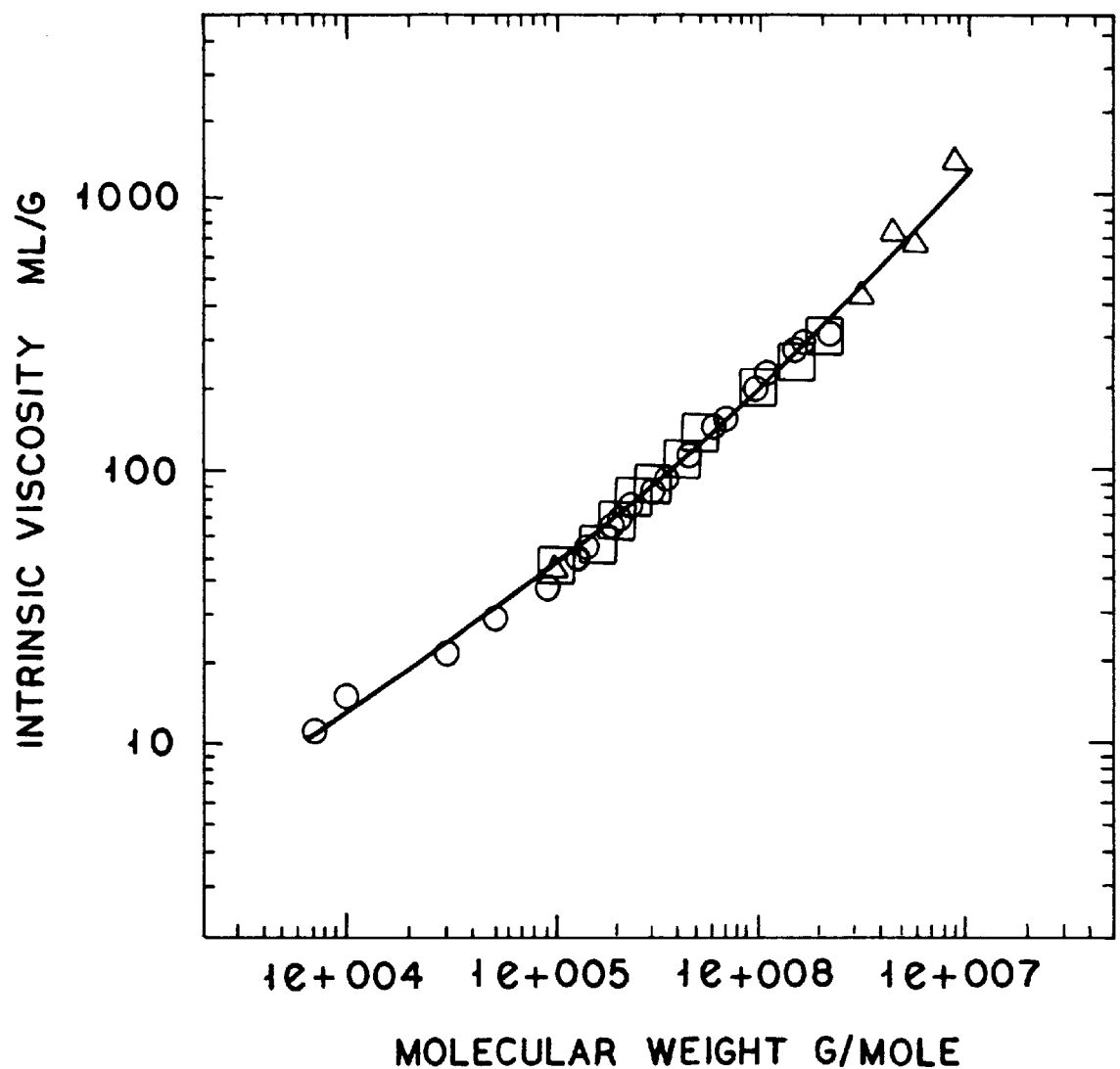
FIG. 3 is a graph showing variation of viscosity with average molecular weight.

In addition, the corresponding molecular sizes were determined by low angle laser light scattering. FIG. 3 is a plot of log intrinsic viscosity versus log $M_W$ for sizes from 7000 to $2 \times 10^6$, for our data (open triangles); the published results of Buliga and Brant, Int. J. Biol. Macromol. 9:71–76, 1987 (open squares), and the results of Kato et al, Biopolymers 21:1623–1633, 1983 (open circles). The published results of Kato shows two linear relationship ships. The low molecular weight pullulan behaves according to the equation $[\eta] = 0.133 M_w^{0.5}$ in ml/g) while the larger molecular weight pullulan behaves according to the equation $[\eta] = 1.9 \times 10^{-2} M_W^{0.67}$ (in ml/g). The Buliga and Brant relation is $[\eta] = 2.58 \times 10^{-2} M_W^{0.646}$ (in ml/g). The best fit curve drawn by visual inspection through all the data gives the equation $[\eta] = 0.12 M^{0.5} + 0.00008 M$.

Viscosities were also determined over a range of higher polysaccharide concentrations for pullulan from strains AP1, AP24, AP30 and commercial pullulan from Hayashibara (PF-20, lot 00228). Viscosity was measured with a Brookfield viscometer at 20° C. at a shear rate of 6.5/sec. The results are set forth in Table 4 and show that the new strains accumulate exopolysaccharide material with higher molecular weight than the preexisting strain AP1.

TABLE 5

| Sample | Concentration g/100 ml | Viscosity cp |
|---|---|---|
| AP1 | 5.0 | 1080 |
| | 2.0 | 38 |
| | 1.0 | 7 |
| AP24 | 5.0 | 13200 |

TABLE 5-continued

| Sample | Concentration g/100 ml | Viscosity cp |
|---|---|---|
| | 2.0 | 460 |
| | 1.0 | 43 |
| AP30 | 5.0 | 30000 |
| | 2.0 | 1660 |
| | 1.0 | 180 |
| PF-20 | 5.0 | 20 |
| | 2.0 | 4 |

Additional Molecular Weight Analysis

A small sample of cells for each strain was removed from the −70° C. freezer, spread on P1 (1% sucrose) agar plates and incubated at 28° C. for 5 days. A "loopful" of cells was added to 2.5 ml of P2 (5% sucrose) liquid medium and shaken overnight to prepare a seed culture. A sample of cells, equal in cell number and about 0.2 ml, was added to each replicate flask containing 15 ml of P2 medium (5% sucrose) and the cultures were shaken at 25° C. for 66 hours. Each sample was diluted with one volume of deionized water, centrifuged, and the polysaccharides were recovered from the clarified broth by precipitation with IPA. The samples were pressed and blotted to remove excess fluid, redissolved with 30 ml of deionized water and then placed in an oven for 1 hour at 100° C. to speed dissolution. As shown by the matrix in FIG. 4, the intrinsic viscosities for pullulan samples from cultures of strains AP2, AP11, AP27 and AP30 were considerably larger than the other pullulan samples. In FIG. 4, the letters refer to the strains as follows: A, AP1; B, AP9; C, AP4; D, AP2; E, AP31; F, AP32; G, AP11; H, AP26; I, AP27; J, AP30; K, AP33; L, AP34; M, AP35 and N, AP36.

Sensitivity or Resistance to Pullulanase

A sample of each rehydrated polysaccharide was analyzed for sensitivity or resistance to the enzyme pullulanase (E.C.

3.2.1.41 from *Enterobacter aerogenes*) by weighing before and after treatment. Six identical samples of 3.0 g of 1% w/v were prepared for each strain and the following was added: 0.6 ml $H_2O$, 0.9 ml 0.5M sodium acetate buffer (pH 5.2) and 60 μl of 3.2M $(NH_4)_2SO_4$ (pH 6.2) buffer with or without 1.6 units of pullulanase. (One unit will liberate 1.0 μmole of maltotriose from pullulan per minute at pH 5.0 at 25° C.) The enzymatic reactions were incubated for 3 hours at 45° C. For each sample 0.56 ml was stored at −20° C. for thin layer chromatography described hereinafter. The remaining 4 ml was precipitated with 1 volume of IPA and then centrifuged at 5000×g for 5 minutes. For the untreated controls, the pellets were dried and weighed. For the enzyme-treated samples the very small precipitates were dissolved in 0.5 ml per sample (dissolution was complete almost instantaneously) and then the triplicate samples were pooled. Each pool was centrifuged at 5000×g for 5 minutes to remove insoluble cell debris and the supernatant precipitated again with one volume of IPA to determine the amount of polysaccharide remaining after enzyme treatment. (The amount of cell debris was significant for samples of AP30 and needed to be subtracted from the IPA-precipitate before calculating pullulanase resistance.) The fraction of pullulanase-resistant material was the weight of polysaccharide following enzyme treatment divided by the weight of polysaccharide with no enzyme treatment. Table 5 shows that the exopolysaccharide made by the new strains is at least 98% pullulanase-sensitive.

TABLE 6

| | IPA precipitate (mg) | | | |
|---|---|---|---|---|
| | AP1 | AP24 | AP30 | PF20 |
| Pullulanase treated (3 samples) (pooled) | 0.7 | 0.0 | 3.3 | 3.3 |
| Not treated (3 samples) | 25.0 | 27.4 | 28.5 | 162.6 |
| | 24.4 | 27.3 | 28.4 | 162.6 |
| | 25.1 | 26.5 | 28.2 | 162.6 |
| Pullulanase resistant fraction (average) | 0.009 | 0.0 | 0.009 | 0.007 |

Chromatographic Detection of Maltotriose

The products from the pullulanase digest were separated by thin layer chromatography to demonstrate the qualitative presence of maltotriose. The thin layer chromatography plates were Art.13145 Kieselgel 60CF245 (10×20 cm with precut channels) from E. Merck, Darmstadt. They were gently soaked overnight immediately before use in a mixture of 0.5M $NaH_2PO4$ and 25% v/v methanol, then air dried and baked for 60 minutes at 100° C., and finally cooled to room temperature before sample application. The previously frozen samples were thawed. A 1 μl sample was loaded onto the TLC plate directly from a 1 μl capillary pipet under a stream of hot air from a handheld hair drier. The samples were flanked by a known mixture of glucose, maltose, maltotriose and maltotetraose. The running buffer was 20 ml IPA, 20 ml acetone, 9.91 ml $H_2O$ and 0.09 ml 85% lactic acid solution. (Based on the 85% stock solution being 11M, this gives a final concentration of 0.1M lactic acid.) The chromatography was carried out for about 4 hours in a sealed glass container. Then the TLC plate was air dried and sprayed with stain prepared as follows: 80 mg of naphthoresorcinol was added to 40 ml ethanol with 0.8 ml concentrated $H_2SO_4$ and stored in the dark. The phosphate treatment and the lactic acid concentration were important for optimal separation of oligo-saccharides of glucose (Hansen, S. A., 1975, Journal of Chromatography 107:224–226). The chromatogram showed that the exopolysaccharide accumulated by the new strains is degraded by pullulanase enzyme to maltotriose subunits, as expected for pullulan.

[1]NMR Analysis of Polysaccharide Structure $^1$H-NMR and $^{13}$C-NMR demonstrated that the polysaccharide prepared from strains AP24 and 30 had the same pullulan structure as did that from strain AP1 and the commercial samples PF-10 and PF-20.

Liquid Chromatography of Acid Hydrolysis Products

Each dissolved polysaccharide sample was hydrolyzed with 6% $H_2SO_4$ at 130° C. for 3 hours to generate monosaccharides. After centrifugation to remove insoluble material, the samples were separated by liquid chromatography. Calculated from the peak areas, the fraction as glucose was 88% for AP1, 81% for AP24, 90% for AP30 and 93% for PF-20.

Measurement of Acidic Polysaccharide

Triplicate samples of 3.0 g of 1% w/v for each strain were incubated at room temperature for 1 hour with an equal volume of 1% (w/v) CTAB (cetyl-trimethyl-ammonium bromide) resuspended in 0.1M sodium phosphate buffer at pH 7. The samples were then centrifuged at 5,000×g for 5 minutes at room temperature to sediment the precipitated acidic polysaccharide. The precipitates were dried and weighed. The supernatant from the centrifugation was precipitated with 1 volume of IPA, dried, weighed and the fraction of acidic polysaccharide was calculated. Table 6 shows that the samples contained less than 2% as contaminating acidic polysaccharide.

TABLE 7

| | Dry weight (mg) | | | |
|---|---|---|---|---|
| Samples | AP1 | AP24 | AP30 | PF20 |
| CTAB precipitate | 0.3 | 0.1 | 0.1 | 0.0 |
| | 0.2 | 0.0 | 0.2 | 0.0 |
| | 0.1 | 0.0 | 0.1 | 0.0 |
| IPA precipitate | 18.8 | 18.8 | 22.3 | 139.3 |
| of CTAB | 17.1 | 18.9 | 20.9 | 136.3 |
| supernatant | 16.6 | 19.1 | 21.2 | 136.1 |
| Acidic EPS fraction | 0.011 | 0.002 | 0.006 | 0.000 |

Example 3.

Production of Pullulan with the Inventive Strains

A. Production of High Molecular Weight Pullulan

Pullulan having molecular weights between about $6 \times 10^6$ to $9 \times 10^6$ was obtained using the following procedure:

A fermentation was carried out in a 5-liter fermentation vessel using P2 as the medium and an initial sucrose concentration of 50 g/l. The temperature of the fermentation was 27° C. The fermentation was carried out for 48 hours and was then terminated. For the first 24 hour period of the fermentation, the broth was agitated at 300 rpm and for the second 24 hour period, the broth was agitated at 600 rpm. The broth was aerated at a rate of 1.0 volume of air per minute throughout the fermentation. The initial pH was 6.8 to 7.0. The fermentations were inoculated using an inoculum of two precultures in the same medium as used for the fermentation, the inoculum containing about 0.6 grams of cells per liter. The pH of the fermentation broth was allowed to decrease naturally during the fermentation. Within about 12 to 18 hours after initiation of the fermentation, the pH of the broth stabilized and remained at essentially the same value until termination of the fermentation. The pullulan yield was measured by first removing cells and then precipitating the polysaccharide in the clarified broth using isopropylalcohol, followed by drying and weighing. Intrinsic viscosity [η] was measured with a Ubbelohde viscometer and the molecular weight was calculated using the equation: $M_w$, =([η]/0.000258)exp1.548.

The parameters of the fermentation for the specific strains and results obtained therefrom, including the molecular weights, are set forth in Table 8.

TABLE 8

|  | Strain | | |
| --- | --- | --- | --- |
|  | AP24 | AP27 | AP42 |
| Initial | | | |
| Sucrose (g/l) | 50 | 50 | 50 |
| pH | 7.0 | 6.8 | 6.9 |
| Cell mass (g/l) | 0.6 | 0.6 | 0.6 |
| After 48 hours | | | |
| Sucrose (g/l) | 6 | 5 | 5 |
| pH | 3.2 | 3.0 | 3.0 |
| Cell mass (g/10)16 | 6.3 | 6.3 | 6.3 |
| Pullulan (g/l) | 25 | 23 | 23 |
| Intrinsic viscosity (dl/g) | 6.7 | 7.8 | 7.6 |
| Molecular weight (x10exp6) | 6.7 | 8.5 | 8.3 |

B. Stabilization of Pullulan Molecular Weight by Adjusting the pH of Culture Broths Separate cultures of strains AP1 and AP30 were grown in baffled Erlenmeyer flasks at 25° C. with shaking. The medium of each was P2 salts (pH 7) plus corn syrup at 5% w/v. After 36, 48, 60 and 72 hours of fermentation, a 25 ml sample was withdrawn from each culture, transferred to a fresh flask, and the pH adjusted to 7.0 with NaOH. The fermentation of the withdrawn samples was continued and the pH was similarly adjusted every 12 hours until the final sample was collected at 72 hours. The intrinsic viscosity of the product was determined, and tabulated below. A shift to pH 7.0 before or at the end of a fermentation caused the intrinsic viscosity to increase. During fermentation of A. pullulans the pH generally drops to about pH 3–4. Therefore, these results indicate that adjusting the pH to neutrality, allows accumulation of pullulan of large molecular weight.

TABLE 9

| Strain | Time of pH adjustment (hours) | Intrinsic viscosity (dl/g) |
| --- | --- | --- |
| AP1 | 36 | 16 |
|  | 48 | 8 |
|  | 60 | 6 |
|  | 72 | 5 |
| AP30 | 36 | 29 |
|  | 48 | 20 |
|  | 60 | 17 |
|  | 72 | 12 |

C. Inactivation by Heating of Pullulan-degrading Enzyme Activity of A. pullulans Experiment 1

A liquid culture of A. pullulans was grown for 4 days at 28° C. with shaking in P2 minimal salts medium containing 0.5% (w/v) corn syrup. The cells were removed by centrifugation at 10,000×g for 10 minutes. The supernatant containing the enzyme was divided into two parts. One part received sodium phosphate to give a final concentration of 0.1 M at pH 7.0, and the other received sodium acetate to give a final concentration of 0.1M at pH 3.7. Each preparation was then heated in a boiling water bath for different durations. After 10 minutes for cooling, 5 ml of heat-treated enzyme was mixed with 15 ml of 1% (w/v) high molecular weight pullulan. At various times, samples were tested for viscosity using a Brookfield LVTDV-II viscometer with the UL spindle at 6 rpm. The results given in Table 10 indicate that both heat treatments resulted in higher viscosities compared to no heat treatments. The results also show that heat treatment conducted at pH 3.7 were more effective at stabilizing viscosity than heat treatments at pH 7.

TABLE 10

| pH | Duration of heat treatment (min) | Viscosity (cp) of pullulan at various times after heat treatment | | | |
| --- | --- | --- | --- | --- | --- |
| | | 1.5 h | 2.5 h | 18 h | 25 h |
| 7.0 | 0 | 64 | 62 | 21 | 17 |
|  | 10 | 74 | 72 | 47 | 42 |
|  | 30 | 70 | 74 | 48 | 40 |
| 3.7 | 0 | 53 | 44 | 14 | 12 |
|  | 70 | 70 | 62 | 52 | 52 |
|  | 30 | 72 | 71 | 70 | 66 |

Experiment 2

An enzyme containing extract was prepared by growing strain AP30 for 96 hours in P2 medium containing 0.5% (w/v) corn syrup. The cells were removed by centrifugation at 10,000×g for 5 minutes and then the supernatant was divided into aliquots and frozen at −70° C. One sample was thawed on ice and then heat treated at various temperatures for different periods of time. The treated extracts (1 ml) were mixed with 1 ml of 2.5% (w/v) Difco potato starch at a pH of 3.7 or 7.0. The hydrolysis of the starch was measured by determining the decrease in absorbance through time at 320 nm. This is a modification of the method for assaying alpha-amylase activity of Virolle, M. J. Morris, V. J. and Bibb, M. J. (1990) Journal of Industrial Microbiology 5:295–302. The results are shown in Table 11 which shows that after heat treatment at 80° C. for one hour, the enzyme has been deactivated as evidenced by the absence of decrease in the absorbance after cessation of the heat treatment.

TABLE 11

| | Treatment duration (hr) temperature | Absorbance at 320 nm at different times after end of heat treatment | | |
| --- | --- | --- | --- | --- |
| pH | (°C.) | 10 min. | 30 min. | 50 min. |
| 7.0 | 2.5 hr/24° C. | 0.48 | 0.32 | 0.27 |
|  | 2.5 hr/37° C. | 0.48 | 0.32 | 0.27 |
|  | 2.5 hr/50° C. | 0.54 | 0.40 | 0.34 |
|  | 2.5 hr/80° C. | 0.65 | 0.64 | 0.65 |
|  | 1 hr/80° C. | 0.63 | 0.61 | 0.62 |
|  | 1 hr/20° C. | 0.68 | 0.67 | 0.67 |
| 3.7 | 2.5 hr/24° C. | 0.49 | 0.35 | 0.29 |
|  | 2.5 hr/37° C. | 0.52 | 0.41 | 0.36 |
|  | 2.5 hr/50° C. | 0.53 | 0.43 | 0.38 |
|  | 2.5 hr/80° C. | 0.57 | 0.56 | 0.56 |
|  | 1 hr/80° C. | 0.61 | 0.60 | 0.62 |
|  | 1 hr/120° C. | 0.63 | 0.62 | 0.62 |

What is claimed is:

1. An isolated substantially biologically pure microbial culture selected from the group consisting of those having the following identifying characteristics: A. pullulans ATCC 74100, A. pullulans ATCC 74101, A. pullulans 74102, A. pullulans 74103, A. pullulans 74104, and A. pullulans 74105, and mutants thereof, said culture being capable of reproducing itself and of producing substantially non-pigmented pullulan having an $M_W$ of at least $6 \times 10^6$ in isolatable amounts when cultured in a liquid growing medium containing assimilable sources of carbon, nitrogen, and inorganic substances.

2. Isolated and substantially biologically pure microbial cultures selected from the group having the following identifiable characteristics: *A. pullulans* ATCC 74100, *A. pullulans* 74101, and *A. pullulans* ATCC 74105, and mutants thereof, said culture being capable of reproducing itself and capable of producing substantially non-pigmented pullulan having an $M_W$ of at least $6 \times 10^6$ in isolatable amounts when cultured under aerobic conditions in a liquid growing medium containing assimilable sources of carbon, nitrogen, and inorganic substances and having the DNA restriction patterns of lanes b, c, and d of FIG. 2B.

* * * * *